(12) United States Patent
De Langen et al.

(10) Patent No.: US 8,835,247 B2
(45) Date of Patent: Sep. 16, 2014

(54) SENSOR ARRAY AND A METHOD OF MANUFACTURING THE SAME

(75) Inventors: Michel De Langen, Beuningen (NL); Ger Reuvers, Eindhoven (NL); Frans Meeuwsen, Heilig Landstichting (NL)

(73) Assignee: NXP, B.V., Eindhoven (NL)

( * ) Notice: Subject to any disclaimer, the term of this patent is extended or adjusted under 35 U.S.C. 154(b) by 975 days.

(21) Appl. No.: 12/992,113

(22) PCT Filed: May 11, 2009

(86) PCT No.: PCT/IB2009/051922
§ 371 (c)(1),
(2), (4) Date: Nov. 11, 2010

(87) PCT Pub. No.: WO2009/138939
PCT Pub. Date: Nov. 19, 2009

(65) Prior Publication Data
US 2011/0062531 A1 Mar. 17, 2011

(30) Foreign Application Priority Data

May 13, 2008 (EP) .................................. 08103938

(51) Int. Cl.
*H01L 21/8242* (2006.01)
*G01N 21/64* (2006.01)
*B01J 19/00* (2006.01)
*B01L 3/00* (2006.01)

(52) U.S. Cl.
CPC ... *G01N 21/6454* (2013.01); *B01J 2219/00364* (2013.01); *B01L 2300/0636* (2013.01); *B01J 2219/00653* (2013.01); *B01J 19/0046* (2013.01); *B01L 2300/0663* (2013.01); *B01J 2219/00529* (2013.01); *B01J 2219/00585* (2013.01); *B01J 2219/00725* (2013.01); *B01J 2219/00722* (2013.01); *B01J 2219/00605* (2013.01); *B01J 2219/00659* (2013.01); *B01L 3/5085* (2013.01); *B01J 2219/00704* (2013.01); *B01J 2219/00315* (2013.01); *B01J 2219/00743* (2013.01); *B01J 2219/00596* (2013.01); *B01J 2219/0074* (2013.01)
USPC ........... 438/241; 438/106; 438/608; 438/618; 257/E21.006; 257/E21.007; 257/E21.051; 257/E21.126; 257/E21.127; 257/E21.17; 257/E21.229; 257/E21.264; 257/E21.267; 257/E21.304; 257/E21.311; 257/E21.329; 257/E21.521

(58) Field of Classification Search
USPC ............. 438/197, 241, 9, 311, 270, 597, 602, 438/603, 604, 612, 106, 608, 680, 692, 438/745; 257/E21.006, E21.007, E21.051, 257/E21.126, E21.127, E21.17, E21.229, 257/E21.264, E21.267, E21.304, E21.311, 257/E21.329, E21.521, 213, 415
See application file for complete search history.

(56) References Cited

U.S. PATENT DOCUMENTS

| | | | |
|---|---|---|---|
| 6,225,059 B1 * | 5/2001 | Ackley et al. ................. | 435/6.12 |
| 6,376,233 B1 | 4/2002 | Wolf et al. | |
| 8,501,122 B2 * | 8/2013 | Shirazi .......................... | 422/553 |
| 8,652,774 B2 * | 2/2014 | Yamamoto et al. ........... | 435/6.1 |
| 8,673,772 B2 * | 3/2014 | Widdershoven ............. | 438/638 |
| 2004/0038388 A1 | 2/2004 | Yamamoto et al. | |
| 2007/0141231 A1 | 6/2007 | Qiu et al. | |

FOREIGN PATENT DOCUMENTS

| | | |
|---|---|---|
| DE | 202005007547 U1 | 7/2005 |
| WO | 02/060575 A2 | 8/2002 |
| WO | 2006/058882 A1 | 6/2006 |
| WO | 2007/012991 A1 | 2/2007 |
| WO | 2008/132656 A2 | 11/2008 |

OTHER PUBLICATIONS

MTX Lab Systems, Inc., "Elisa Plate Readers Great Deals Microplate Readers," retrieved from internet web address http://mtxlsi.com/platereaders.htm (Feb. 18, 2008).
International Search Report and Written Opinion for Int'l. patent appln. No. PCT/IB2009/051922 (Jul. 29, 2009).

* cited by examiner

*Primary Examiner* — David Nhu

(57) ABSTRACT

A sensor array for detecting particles, the sensor array comprising a substrate having a plurality of holes, a plurality of electronic sensor chips each having a sensor active region being sensitive to the presence of particles to be detected, and an electric contacting structure adapted for electrically contacting the plurality of electronic sensor chips, wherein the plurality of electronic sensor chips and/or the electric contacting structure are connected to the substrate in such a manner that the plurality of holes in combination with the plurality of electronic sensor chips and/or the electric contacting structure form a plurality of wells with integrated particle sensors.

19 Claims, 3 Drawing Sheets

SENSOR ARRAY AND A METHOD OF MANUFACTURING THE SAME

CROSS-REFERENCE TO RELATED APPLICATIONS

This application is a 371 of PCT/IB09/51922 FILED Mar. 11, 2009; European Patent Office 0813938.0 filed May 13, 2008.

FIELD OF THE INVENTION

The invention relates to a sensor array.

Moreover, the invention relates to a method of manufacturing a sensor array.

BACKGROUND OF THE INVENTION

A biosensor may be denoted as a device which may be used for the detection of an analyte and may combine a biological component with a physicochemical or physical detector component.

For instance, a biosensor may be based on the phenomenon that capture particles immobilized on a surface of a biosensor, may selectively attach with target particles in a fluidic sample, for instance when an antibody-binding fragment of an antibody or the sequence of a DNA single strand as a capture particle fits to a corresponding sequence or structure of a target particle. When such attachment or sensor events occur at the sensor surface, this may change the optical properties of the surface which can be detected as the sensor event.

WO 2007/012991 discloses an interconnection and packaging method for manufacturing of Lab-on-chip (LOC) and Micro Total Analyses Systems. Different functions, such as biosensors, heaters, coolers, valves, and pumps, are combined in an electronic/mechanical/fluidic module by flip-chip technology using an ultrasound bonding process. A predefined polymeric ring on the chip serves as a seal.

Conventional methods for manufacturing sensors may be complex.

OBJECT AND SUMMARY OF THE INVENTION

It is an object of the invention to provide a sensor being manufacturable with reasonable effort.

In order to achieve the object defined above, a sensor array and a method of manufacturing a sensor array according to the independent claims are provided.

According to an exemplary embodiment of the invention, a (for instance two-dimensional) sensor array (particularly a biosensor array) for detecting particles is provided, the sensor array comprising a substrate (which may be a rigid electrically insulating plate) having a plurality of holes (for instance through holes or blind holes, which holes may be arranged in a two-dimensional manner), a plurality of electronic sensor chips (such as monolithically integrated semiconductor circuits) each having a sensor active region (for instance a biological interface) being sensitive to the presence of particles to be detected (for example, each of the sensor active regions may be sensitive specifically to a different type of particles), and an electric contacting structure adapted for electrically contacting (for instance each of) the plurality of electronic sensor chips (for instance via electrically conductive bumps and/or via electrically conductive wires), wherein the plurality of electronic sensor chips and/or the electric contacting structure are connected (for instance mechanically and/or electrically) to the substrate in such a manner that the plurality of holes in combination with the plurality of electronic sensor chips and/or the electric contacting structure form a plurality of wells with/having integrated particle sensors (for instance each of the holes in combination with an assigned one of the sensor chips may form a well for receiving a fluidic sample being analyzable by the sensor located within the well).

According to another exemplary embodiment of the invention, a method of manufacturing a sensor array for detecting particles is provided, the method comprising forming a substrate having a plurality of holes, forming a plurality of electronic sensor chips each having a sensor active region being sensitive to the presence of particles to be detected, forming an electric contacting structure adapted for electrically contacting (for instance each of) the plurality of electronic sensor chips, and connecting the plurality of electronic sensor chips and/or the electric contacting structure to the substrate in such a manner that the plurality of holes in combination with the plurality of electronic sensor chips and/or the electric contacting structure form a plurality of wells with integrated particle sensors.

The term "sensor array" may particularly denote an arrangement of a plurality of sensors, for instance in a regular pattern. The number of sensors of such a sensor array may be larger than two, particularly larger than ten, more particularly larger than one hundred. An example for such a sensor array may be a microtiter plate having a number of wells each providing a sensor function and being arranged in a matrix-like manner.

The term "sensor" may particularly denote any device which may be used for the detection of an analyte. Examples for sensors which may be realized according to exemplary embodiments are gas sensors, smoke sensors, biosensors, pH sensors, humidity sensors, etc. According to an embodiment, the sensor principle may be an electric sensor principle, that is may detect particles on the basis of an electric measurement.

The term "biosensor" may particularly denote any device which may be used for the detection of a component of an analyte comprising biological particles such as DNA, RNA, proteins, enzymes, cells, bacteria, virus, etc. A biosensor may combine a biological component (for instance capture particles at a sensor active surface capable of detecting particles) with a physicochemical or physical detector component (for instance a capacitor having an electric characteristic which is modifiable by a sensor event).

The term "electronic sensor chip" may particularly denote a sensor built with the help of micro- or nano-technologies like lithography, etch or deposition techniques. It may particularly denote a monolithically integrated circuit, that is to say as an electronic chip or die, particularly in semiconductor technology, more particularly in silicon semiconductor technology, still more particularly in CMOS technology. A monolithically integrated sensor chip has the property of very small dimensions due to the use of micro- or nano-processing technology, and may therefore have a large spatial resolution and a high signal-to-noise ratio. A sensing principle of such an electronic chip may be based on an electric measurement such as an ohmic resistance, a capacity, etc. which may be sensitively modified upon a sensor event.

The term "sensor active region" may particularly denote a region of a sensor which may be functionally coupled with a fluidic sample so that a detection event may occur in vicinity of the sensor active region. In other words, the sensor active region may be influenced by processes which take place in case of a sensing event. A corresponding sensing principle may be an indirect electrical sensing principle (that is a change of the electric properties of the sensor active region).

The term "substrate" may denote any suitable material, such as a semiconductor, glass, plastic, etc. According to an exemplary embodiment, the term "substrate" may be used to define generally the elements for layers that underlie and/or overlie a layer or portions of interest. Also, the substrate may be any other base on which a layer is formed. Furthermore, a substrate may provide walls delimiting at least a part of a fluidic well.

The term "fluidic sample" may particularly denote any subset of the phases of matter. Such fluids may include liquids, gases, plasmas and, to some extent, solids, as well as mixtures thereof. Examples for fluidic samples are DNA containing fluids, cells containing fluids, blood, interstitial fluid in subcutaneous tissue, muscle or brain tissue, urine or other body fluids. For instance, the fluidic sample may be a biological substance. Such a substance may comprise proteins, polypeptides, nucleic acids, DNA strands, etc.

The term "particle" may particularly denote a molecule, an organic molecule, a biological particle, DNA, RNA, a protein, an amino acid, a bead, a nano-bead, a nano-tube, etc.

The term "biological particles" may particularly denote any particles which play a significant role in biology or in biological or biochemical procedures, such as genes, DNA, RNA, proteins, enzymes, cells, bacteria, virus, etc.

According to an exemplary embodiment of the invention, an arrangement of a plurality of sensors for fluidic analysis purposes may be provided in which a substrate having multiple holes can be bonded to multiple monolithically integrated sensor chips operating in accordance with an electric sensing principle and electrically connected via an electric contacting structure to one another. A mechanical connection between substrate and dies may be adjusted such that wells may be formed having sidewalls which are defined by the sidewalls of the holes in the substrate, and having a bottom wall formed at least partially by the sensor chip. Thus, a lightweight self-sufficient and miniaturized sensor array may be provided being manufacturable with reasonable cost and allowing to be operated without any further component.

Next, further exemplary embodiments of the sensor array will be explained. However, these embodiments also apply to the method.

The plurality of holes may be through holes (or through drilling or clearance holes or via holes). Thus, a plurality of through holes may be formed to extend through the entire substrate which through holes may comprise side walls but may be free of a closed bottom, wherein an open bottom of each of the through holes may be closed by a corresponding one of the sensor chips. Hence, it may be possible to form a multiple well comprising sensor array with low cost and high performance, since the exposed surface portions of the sensor chips may simultaneously serve for sensing purposes and as bottom walls for spatially delimiting the well (which may accommodate a fluidic sample). Alternatively, the plurality of holes may be blind holes, that is to say holes having a bottom wall at which the sensor chips may be connected.

Each of the plurality of electronic sensor chips may be adapted for evaluating a sensor signal provided by the sensor active region generated in response to the presence of the particles to be detected. Thus, on chip and very close to the sensor event, signal processing may be performed in each of the wells so that complex external processing resources may be omitted. If desired, the pre-processed or readily processed sensor signal may be supplied to a connected external entity, for instance for further evaluation or display to a user.

A surface of each of the plurality of electric sensor chips may form (partially or entirely) a bottom of a respective one of the plurality of wells. Thus, the sensor chip may serve simultaneously as a sensor active region comprising portion at which the actual sensor event is detected, as a monolithically integrated circuit for signal processing, and as a fluidic sample delimiting element forming a portion of a well.

The electric contacting structure may be adapted for electrically interconnecting different ones of the plurality of electronic sensor chips. For example, such an electrical contacting structure may be a patterned electrically conductive member forming traces for contacting different ones of the electric sensor chips, and may also supply electric signals to an external interface of the sensor array for supply to a coupled entity, for instance for further processing.

The electric contacting structure may be adapted as a patterned foil (which may be flexible and which can be electrically insulating) comprising electrically conductive traces (which may be formed as a patterned electrically conductive layer on the foil). Thus, a thin planar foil may be provided which can be patterned so as to provide a specific electric contacting performance. This may allow for a lightweight construction of the sensor array having a proper electric performance. The patterned foil may have recesses each aligned for exposing a sensor active region of a sensor chip connected to the electric contacting structure in such a manner that contacting portions of the conductive traces are spatially aligned with and electrically coupled (for instance via soldering bumps and/or metal wires) to contact pads of corresponding sensor chips.

The sensor array may comprise one or more bumps (for example solder bumps) and/or one or more wires (for example metal wires) for electrically coupling the electric contacting structure to the plurality of electronic sensor chips. For example, solder bumps may be provided for providing such a proper electric coupling, and at the same time mechanically bonding the two components to one another.

A sealing element may be provided for sealing an interface between the electric contacting structure and the plurality of electronic sensor chips. Hence, a fluidic sample accommodated in one of the wells may be safely prevented from leaking into gaps between the sensor die and the foil/traces arrangement. Such a sealing element may have the capability of providing a fluidic sealing so that a fluidic sample inserted into the well may remain there and may be securely prevented from flowing into the electrically conductive portions in which liquids may have a deteriorating effect. Such a sealing element may be provided as an annular sealing element. Such a sealing element may be made of a polymeric material.

The sensor array may comprise a communication interface, particularly a Universal Serial Bus (USB) interface, electrically coupled to the electric contacting structure. Thus, signal provided and processed by the electric sensor chips and conducted via the electric contacting structure may be supplied to a coupled entity such as a communication partner device. Such a communication partner device may be a computer (such as a laptop) at which the sensor results may be further evaluated. In an alternative embodiment, the sensor array may be completely self-sufficient so that no coupling with an external entity is necessary. However, in an embodiment in which a communication interface is present, the coupled entity such as a personal computer may further process the sensor results and/or display them to a user via a GUI (Graphical User Interface). The communication between the sensor array and the communication partner device may be a wired connection (such as in an embodiment with a USB interface), or may be a wireless communication (for instance using Bluetooth, infrared communication or radio frequency communication).

The substrate may be a rigid plate, for example a rectangular or square plate. For instance, the substrate may be a flat plate which cannot be bent. The substrate may be made of a plastic material or of a glass material. The substrate may have a length of several centimeters (for instance 3 cm to 20 cm), may have a width of several centimeters (for instance 3 cm to 20 cm), and may have a thickness being smaller than the length and the width (for instance less than 1 cm). The holes in the substrate may have a length and a width of several millimeters and may extend through a part of the thickness of the substrate or through the entire thickness of the substrate.

Each of the plurality of sensor active regions may comprise one or more capture molecules. Such capture molecules may be oligonucleotide sequences which are immobilized at the sensor active region and may have the capability of selectively hybridizing with specific particles to be detected. Such a hybridization event may then change the electric properties in an environment of the sensor active region which may be detected electrically.

The sensor array may be adapted as a biosensor array. In other words, the sensor array may be adapted for detecting biological particles such as DNA, proteins, cells, viruses, polypeptides, polynucleotides, hormones, viruses, bacteria, etc.

The sensor array may be adapted as a microtiter plate. Such a microtiter plate may be a matrix-like arranged array of sensors, for instance 96 or 384. With such a microtiter plate, it is possible to perform high throughput analysis in pharmacological research or to perform medical measurements by a user.

The sensor array may be adapted as a self-sufficient operable sensor array. Thus, no coupling to a further entity such as an external reader device may be necessary, since all the signal processing and signal evaluation tasks may be performed within the sensor array. The sensor array may also be adapted as a portable sensor array. This may make the sensor array appropriate for being used even by an unskilled user such as a patient.

In the following, further exemplary embodiments of the method will be explained. However, these embodiments also apply to the sensor array.

In one embodiment, the method may comprise mounting the plurality of electronic sensor chips on the electric contacting structure (for instance on a flexible foil having electrically conductive traces) to thereby form a continuous contacted chip arrangement (this may be done by flip chip technology or wire bonding), and subsequently connecting the continuous contacted chip arrangement to the substrate. Thus, it is possible that the manufacturing method includes a chip on foil technology.

In another embodiment, the method may comprise forming the electric contacting structure on the substrate (for instance by deposition and patterning an electrically conductive layer such as a transparent electrically conductive layer like indium tin oxide, ITO) to thereby form a continuous contacted substrate arrangement, and subsequently mounting the plurality of electronic sensor chips on the continuous contacted substrate arrangement. This may also be denoted as a flip chip technology. This method may comprise manufacturing the sensor array using a flip chip on glass technology. In the context of such a flip chip on glass technology, it is possible to provide holes in a glass plate to give access to liquids/biomolecules to reach a sensor.

In still another embodiment, the method may comprise moulding the electric contacting structure into/onto a material (such as plastic) constituting the substrate to thereby form a continuous contacted substrate arrangement, and subsequently mounting the plurality of electronic sensor chips on the continuous contacted substrate arrangement. In this embodiment, the substrate may be formed by moulding, simultaneously embedding the electric contacting structure in a manner that electric traces of the electric contacting structure may remain exposed at a surface of the resulting arrangement to form a basis for a subsequent die mounting procedure. It is also possible to implement MID (Moulded Interconnect Devices) technology for the manufacturing. In this context, a moulding process may be implemented for the manufacturing. For example, the electric contacting structure may be moulded into plastic material, exposing electrically conductive portions of the electric contact structure. Then, the electronic sensor chips may be mounted on the moulded carrier.

In an embodiment, a package for sensors may be provided. This aspect of the invention relates to a package for sensor ICs, particularly biosensor ICs. The package comprises or consists of a substrate carrying the sensor dice. Additional ICs can be added to the substrate such as controller ICs, interface ICs and/or RFID ICs. An embodiment of the invention uses technology comparable to Flip Chip on foil technology, as used for LCD drivers. An embodiment of the invention also uses wire bonding technology as used in thin Ball Grid Array (BGA) packages.

Conventionally, standard IC packaging technology is completely covering the IC and shielding it from the environment. New sensing technologies may require the IC to be exposed to the outside world. An embodiment of the invention makes it possible to make part of the IC accessible from the outside, while keeping the remaining sealed from the hostile environment like liquids or gases.

Biological laboratories are using so called microplates (see FIG. 6) to do the testing. Each well in the microplate may contain a biological sample, which need to be tested by the sensors. Accessing each well, one at a time, increases measuring time and lowers productivity of lab personnel and lab equipment. Embodiments of the invention provide a solution for this problem. Such an embodiment may make it possible, for an IC, to have contact with liquids or gases outside the IC package. This is achieved either via a hole in the substrate and/or via an opening in the encapsulant, used to seal the critical parts of the sensor from the environment. Such a design of the substrate may allow a multitude of wells to be measured simultaneously.

In contrast to conventional approaches based on hermetic sealing of the IC from the environment, embodiments of the invention may have part of the IC exposed to the outside world for the sensor to work. Also, embodiments of the invention may use an encapsulant which may be compatible to most biological systems and biological active molecules, such as PDMS also denoted as silicone. An advantage of such a solution is the simple, fairly standard way of processing.

The sensor chips may be monolithically integrated on the basis of a semiconductor substrate, particularly comprising one of the group consisting of a group IV semiconductor (such as silicon or germanium), and a group III-group V semiconductor (such as gallium arsenide).

The sensor chip or microfluidic device may be or may be part of a sensor device, a sensor readout device, a lab-on-chip, an electrophoresis device, a sample transport device, a sample mix device, a sample washing device, a sample purification device, a sample amplification device, a sample extraction device or a hybridization analysis device. Particularly, the biosensor or microfluidic device may be implemented in any kind of life science apparatus.

For any method step, any conventional procedure as known from semiconductor technology may be implemented. Forming layers or components may include deposition techniques like CVD (chemical vapour deposition), PECVD (plasma enhanced chemical vapour deposition), ALD (atomic layer deposition), or sputtering. Polishing may include CMP (chemical mechanical polishing). Removing layers or components may include etching techniques like wet etching, plasma etching, etc., as well as patterning techniques like optical lithography, UV lithography, electron beam lithography, etc.

Embodiments of the invention are not bound to specific materials, so that many different materials may be used. For conductive structures, it may be possible to use metallization structures, silicide structures or polysilicon structures. For semiconductor regions or components, crystalline silicon may be used. For insulating portions, silicon oxide or silicon nitride may be used.

The sensor chip may be formed starting with a purely crystalline silicon wafer or an SOI wafer (Silicon On Insulator).

Any process technologies like CMOS, BIPOLAR, BICMOS may be implemented.

The aspects defined above and further aspects of the invention are apparent from the examples of embodiment to be described hereinafter and are explained with reference to these examples of embodiment.

BRIEF DESCRIPTION OF THE DRAWINGS

The invention will be described in more detail hereinafter with reference to examples of embodiment but to which the invention is not limited.

DESCRIPTION OF EMBODIMENTS

Figure 1:
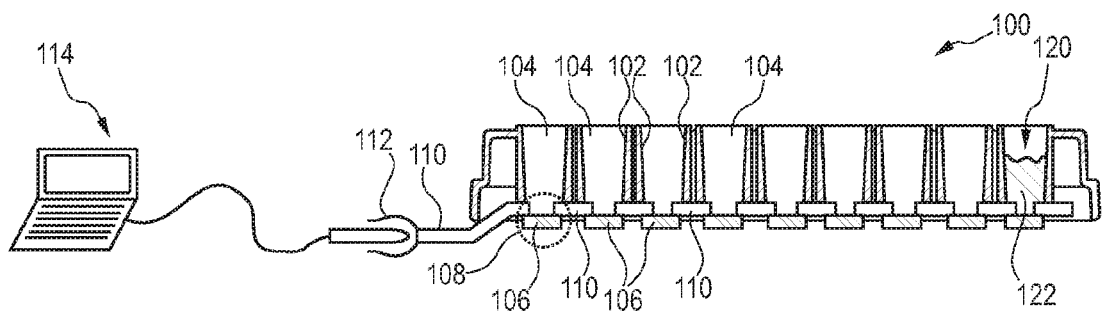
FIG. 1 illustrates a cross-section of a biosensor microtiter plate according to an exemplary embodiment of the invention.

The illustration in the drawing is schematical. In different drawings, similar or identical elements are provided with the same reference signs.

In the following, referring to FIG. 1, a biosensor array 100 for detecting biological particles according to an exemplary embodiment of the invention will be explained.

The biosensor array 100 comprises a plastic substrate 102 having a plurality of matrix-like arranged through holes 104. A plurality of monolithically integrated electronic biosensor chips 106 are provided each being equipped with a sensor active region 202 (compare FIG. 2) sensitive to the presence of biological particles to be detected.

An electrically conductive contacting structure 110 is provided for electrically contacting each of the plurality of the monolithically integrated electronic biosensor chips 106. The monolithically integrated electronic biosensor chips 106 and the electric contacting structure 110 are connected to the glass substrate 102 in such a manner that the plurality of through holes 104 in combination with the correspondingly aligned plurality of monolithically integrated electronic sensor chips 106 and the electric contacting structure 110 form a plurality of wells. In each of the wells, a fluidic sample may be inserted for instance via a pipette or via an automatic pipetting robot. Each of the wells may serve as a fluid container for accommodating a specific fluidic volume of, for instance, 1 ml. Each of the monolithically integrated electronic biosensor chips 106 is adapted for evaluating a sensor signal provided at the sensor active region 202 and generated in response to the presence of the particles to be detected.

One of the wells is indicated schematically with reference numeral 120 in FIG. 1, and is filled with a fluidic sample 122.

FIG. 1 indicates a portion 108 related to a coupling region between the components 106, 110, 102 which will be explained below in more detail referring to FIG. 2.

Figure 2:
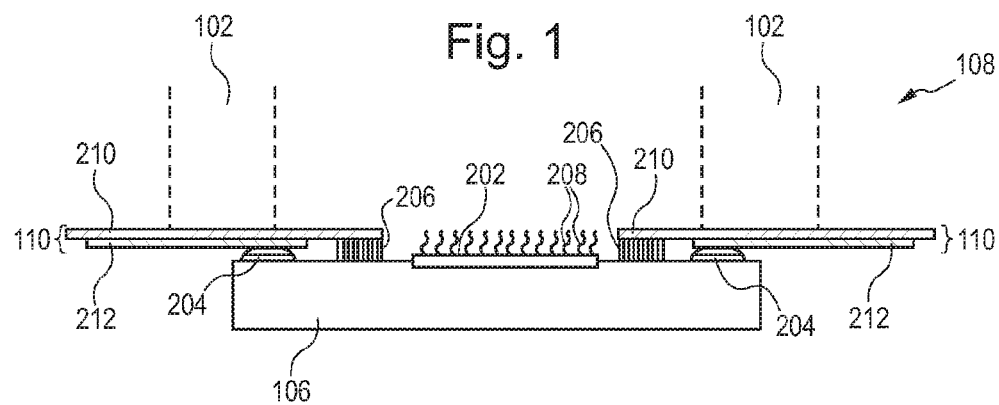
FIG. 2 shows an enlarged view of a portion of the sensor array of FIG. 1.

As can be taken from FIG. 2, a plurality of capture molecules 208 such as single-stranded DNA molecules are immobilized on or as part of the sensor active region 202. In the presence of particles having a sequence which is complementary to the sequence of the capture molecules 208, hybridization events may occur close to the sensor active region 202 which modifies the electrical properties in an environment of the sensor active region 202. Consequently, monolithically integrated circuit components (such as field effect transistors) within the IC 106 may detect a corresponding electric signal which may be evaluated partially or entirely within the IC 106. Thus, the monolithically integrated biosensor chips 106 evaluates a sensor signal provided by the sensor active region 202 generated in response to the presence of the particles to be detected.

Again referring to FIG. 2, a surface of each of the plurality of monolithically integrated electronic sensor chips 106 forms a bottom of a respective one of the plurality of wells. FIG. 2 further shows that the electric contacting structure 110 comprises a patterned foil 210 and electric traces 212 coupled to the monolithically integrated sensor chips 106 via bumps 204. FIG. 2 shows a construction of the sensor die 106 assembled to the foil 210. The electric contacting structure 110 can be connected to a dedicated measurement equipment, or the electric contacting structure 110 can be equipped with a standard USB bus 112 to connect directly to a personal computer 114, as will be explained below.

Furthermore, a polymer seal 206 adapted as an annular plastic ring seals an interface between the electric contacting structure 110 and the monolithically integrated electronic sensor chips 106. In case that a fluid is present on the sensor active region 202, the seal 206 prevents this fluid from flowing towards the electrically conductive components.

Coming back to FIG. 1, signals provided at the electric contacting structure 110 may be supplied to a USB interface 112 (only shown schematically in FIG. 1) of the biosensor array 100. Thus, the sensor result may be provided at this USB interface 112 for monitoring or further processing by a connectable personal computer 114 to which the signals are supplyable via the USB interface 112.

The microtiter plate sensor array 100 of FIG. 1 and FIG. 2 is a self-sufficient operable portable sensor array. Thus, all necessary processing capabilities may be provided within the IC chips 106 so that the final result of the detection can be supplied at the interface 112. No further processing is necessary via the computer 114. However it is possible that such further processing occurs in the computer 114.

According to an exemplary embodiment of the invention, an intelligent microarray plate 100 with integrated biosensors 106, 202 is provided. In other words, a system comprising an intelligent microplate 100 is provided for use in biochemical diagnostics. The microplate 100 may integrate the wells 120 for biological liquids 122 as well as the sensors 106, 202 to measure biologically active components in interfacing electronics. Thus, complex readers for detecting biological molecules utilizing luminescence or fluorescence to detect the molecules may be dispensable according to exemplary embodiments of the invention.

Conventional detection methods for biological molecules use separate readers to detect the molecules. These readers are often very expensive and stationary, thereby making them difficult for use for small hospitals and in developing countries. Methods to readout a plate are relatively slow, resulting in a long delay between sample taking and feedback to the patient (or doctor). A major cost in in vitro diagnostics is manpower. Making the detection a batch process where several wells are checked in parallel decreases the time that an operator has to spend on each liquid and saves money.

Sensors are functionalized in order to detect the set of molecules in parallel, but it is sometimes not taken equally possible to functionalize a single sensor with all the wanted molecules. Having multiple sensors in parallel in a microarray can solve this problem, each functionalized for a different set of molecules.

According to an exemplary embodiment of the invention, it is possible to integrate the detection functionality into the microarray plate 100. The microarray plate 100 can be made of glass, plastic, using MID technology or any combination of these technologies. These technologies also give the possibility to include any desired integrated circuit 106 into the product, for instance for communication or data processing, thereby increasing the intelligence of the system.

Embodiments of the invention may be adapted as microplates for instance being available with 96, 384, 1536 or more wells. The outer dimensions of the microplates may be fixed, which means that the diameter of the wells may be reduced by a factor 2 for every step (9 mm, 4.5 mm, 2.25 mm).

Figure 6:
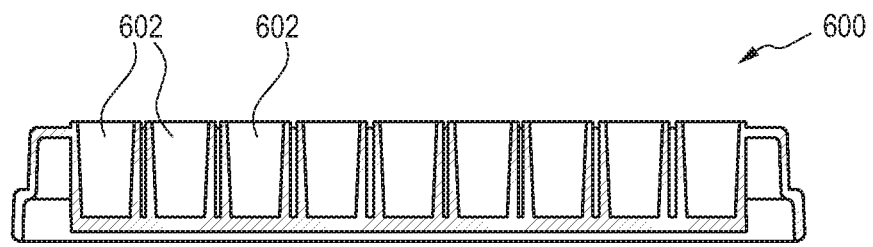
FIG. 6 illustrates a conventional microtiter plate.

Conventionally, after filling wells 602 in a microplate 600 shown in FIG. 6 with the sample and reagent, the microtiter plate 600 is put into a reader system. Reader systems are measuring the fluorescence or luminescence light emitted by tracer molecules in the solution. The amount of light is a measure of the amount of biomolecules in the solution. In biological laboratories, extensive use is made of the standardized plates 600 with wells 602 to perform biochemical analysis.

In contrast to the conventional approach of FIG. 6, exemplary embodiments of the invention use biosensor integrated circuits 106 which can be mounted on a flexible substrate 110, and the flexible substrate 110 may be mounted on a bottom of a microplate 102. The microplate 102 may be specifically designed for this process. The bottom of the wells 120 in the microplate 102 may be removed, giving the liquid 122 in the wells 120 direct contact with the sensors 106, 202, compare FIG. 1 and FIG. 2.

Figure 3:
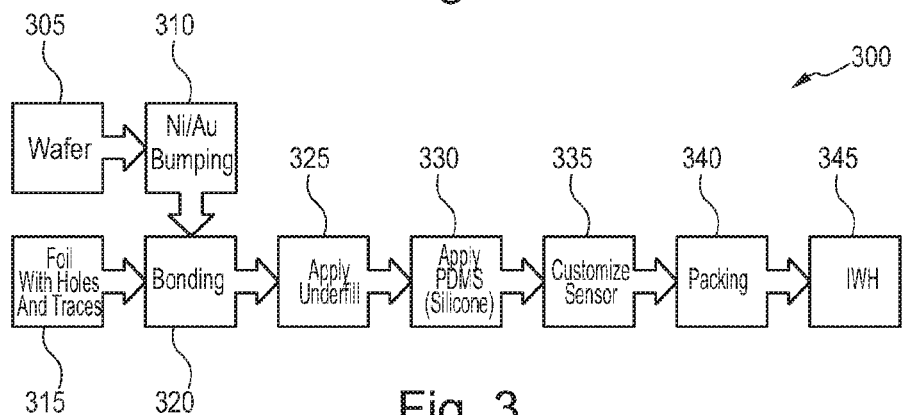
FIG. 3 is a flow-chart illustrating a method of manufacturing a sensor array according to an exemplary embodiment of the invention.

FIG. 3 shows a flow-chart 300 illustrating a method of manufacturing a biosensor array 100 as shown in FIG. 1 and FIG. 2.

In a block 305, a wafer is processed to manufacture the monolithically integrated biosensor chips 106. A nickel and/or gold bumping 204 may be applied to the IC 106 in a block 310. In a block 315, a foil 210 may be patterned to have holes and to have traces 212. In a block 320, a bonding between the bumped IC 106 and the electric conduction structure 110 is performed. In a block 325, an underfill may be applied, and in a block 330, PDMS (Poly Dimethyl Siloxane, silicone) may be applied. In a block 335, the sensor may be customized. A packing procedure, see block 340 may be performed as well, and the manufacture procedure may be finished in a block 345. Thus, FIG. 3 illustrates a process flow for manufacturing a flex circuit.

As an alternative to the flip chip procedure described referring to FIG. 1 to FIG. 3, it is also possible to use wire bonding to interconnect the integrated circuits 106 to the flex 210.

After the foil 210 is manufactured, it can be attached to the bottom of the microplate 102, for instance by glueing.

Figure 4:
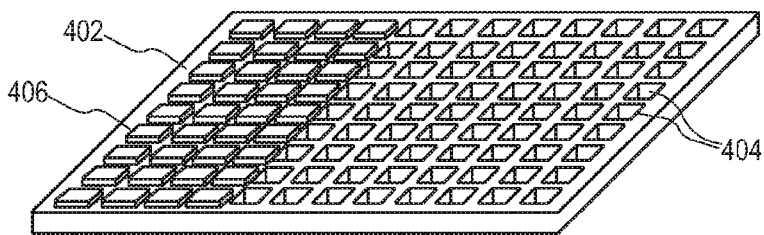
FIG. 4 illustrates a sensor array according to another exemplary embodiment of the invention.

Referring to FIG. 4, another way to produce a microplate 400 with integrated sensor chips 406 is by using a glass plate 402 having a pattern of through holes 404. FIG. 4 illustrates the glass microplate with the sensor chips 406 from the backside. This allows to manufacture the sensor array 400 according to another exemplary embodiment of the invention.

In the embodiment of FIG. 4, the holes 404 are made in the glass plate 402, for instance by powder blasting. After the hole formation, the glass plate 402 may be patterned with ITO (Indium Tin Oxide) traces (not shown) to provide interconnection between the different sensors 406. The sensors 406 are subsequently bonded on the glass plate 402, for instance using thermosonic or flip chip bonding.

Another way to make the plates is using a moulding process. For this purpose, a foil may be manufactured holding the traces for the interconnection of the sensors. The foil is moulded into plastic in such a way that the traces are on the outer side of the plastic. The sensors are mounted on the plastic carrier using thermosonic bonding or using (conductive) adhesive. Such a technology may be denoted as an MID (Moulded Interconnect Device) technology for manufacturing a biosensor array.

According to an exemplary embodiment of the invention, a sensor may be provided which uses differences in electric properties to measure the presence of biomolecules instead of light. Such an electronic measurement may be preferred over an optical measurement. It may give advantages in processing a collection of data.

Embodiments of the invention may use materials which are complying with liquids used in test samples.

Embodiments of the invention can be easily interfaced with a standard PC, as shown in FIG. 1. This makes the readout simple and does not need large investment in hardware. It may also be possible to implement the sensor array for mobile healthcare applications. When the data evaluation is done on a PC, this may give the opportunity for a detailed statistical analysis and study using measurement data of different patients. It also allows interfacing to a digital patient dossier in a simple manner.

Figure 5:
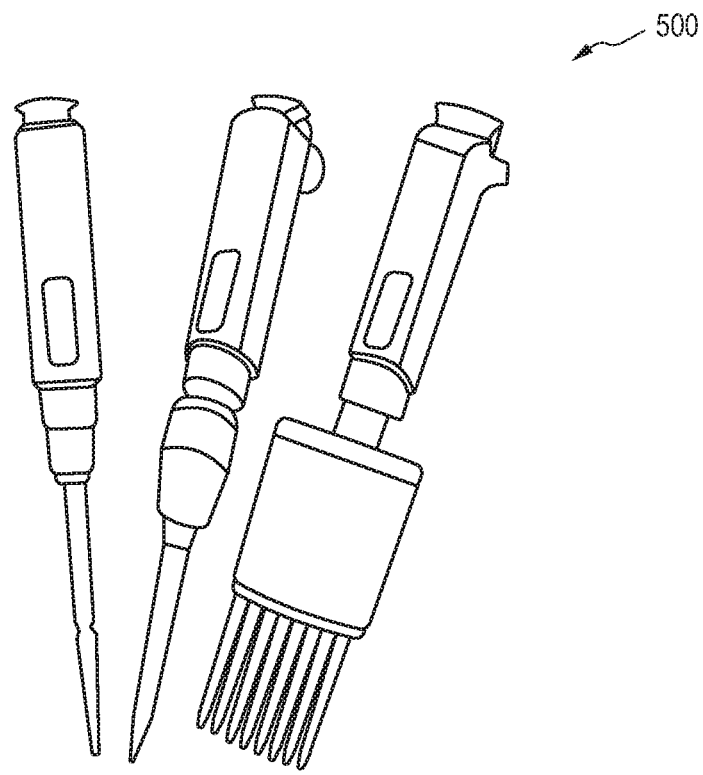
FIG. 5 illustrates micropipettes for use with a sensor array according to an exemplary embodiment of the invention.

Another advantage of embodiments of the invention is that this concept matches to standard dimensions of microplates. Therefore, standard micropipettes 500 as shown in FIG. 5 with multiple heads may be used together with embodiments of the invention, and standard equipment may be used to fill fluidic sample into the wells. Thus, there is no need to develop new expensive tools.

Figure 7:
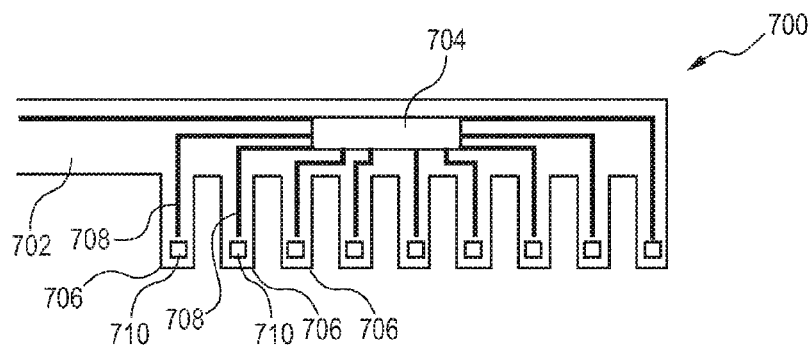
FIG. 7 illustrates an array of biosensors and a control or interface IC for usage in a standard microtiter plate according to an exemplary embodiment of the invention.

An exemplary field of application of embodiments of the invention are diagnostic systems. These may be for single use or may form part of a larger system. Such diagnostics may allow to determine biochemical molecules, for instance to perform DNA sequencing. A sensor package 700 according to another embodiment of the invention shown in FIG. 7 may use a substrate 702 to carry a control or interface die 704. The substrate 702 can be made of polyamide or more traditional PCB (Printed Circuit Board) materials like BT (Bismaleimide-Triazine) epoxy, FR4 (Flame Retardant 4) or FR5. The substrate 702 is designed with a number of fingers 706 to give the package 700 access to a column of wells in the microplate (compare FIG. 1, FIG. 4 or FIG. 6). Each finger 706 has an assigned electric connection element 708 and a sensor active region 710. Thus, one IC 704 may serve simultaneously a number of sensor active regions 710, eight in the present embodiment. A decoupling capacitor (not shown) or another electronic element may also be attached and connected to the substrate. For a 96 well SBS microplate the number of fingers may be eight, for a 384 well plate 16 and so on. FIG. 7 shows a substrate 702 with biosensors which can be put into a microtiter plate.

A sensor package according to an exemplary embodiment of the invention can be made using flip chip technology or wire bonding technology. In case of flip chip technology, the Flip chip process flow of FIG. 3 can be used. In this flow, several processing choices need to be made. For instance, electrolytic gold bumping, copper bumping or even solder bumping can replace the Ni/Au bumping.

Figure 8:
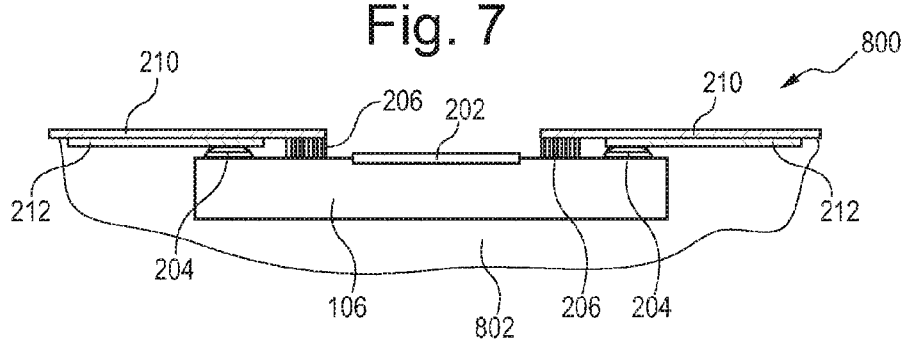
FIG. 8 illustrates a partially exposed and partially encapsulated sensor chip according to an exemplary embodiment of the invention.

Using such a flow, a packaged sensor 800 according to an exemplary embodiment of the invention may be made, as shown in FIG. 8. FIG. 8 shows a flip chip construction of the packaged sensor 800.

In addition to the members shown in FIG. 2, the embodiment of FIG. 8 includes additionally an encapsulant 802 which can be made of, but is not limited to, PDMS (Polydimethylsiloxane, silicone). This may have the advantage of being neutral to most used biological materials and fluids.

Figure 9:
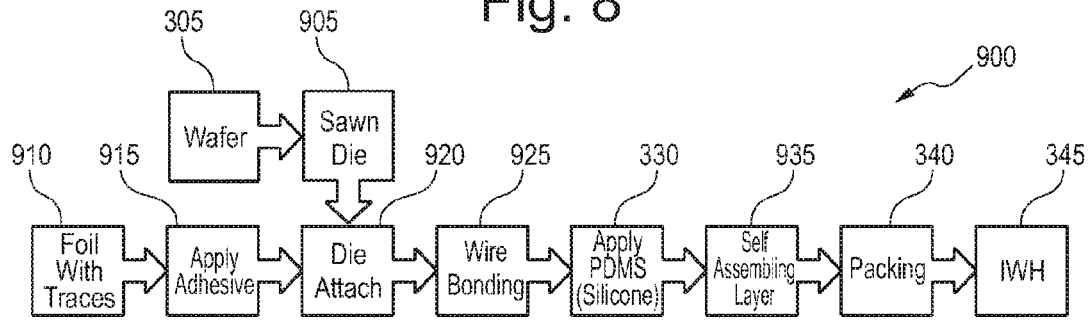
FIG. 9 is a flow-chart illustrating a method of manufacturing a sensor according to an exemplary embodiment of the invention.

In the case wire bonding is used as the assembly process, the flow may be different. FIG. 9 shows a possible processing flow 900 for this process.

In a block 305, a wafer is processed to manufacture monolithically integrated biosensor chips 106. In a block 905, the die 106 may be sawn. In a block 910, a foil 210 may be provided with traces 212. In a block 915, adhesive may be applied. In a block 920, a die attachment is performed. In a block 925, wire bonding may be performed, and in a block 330, PDMS (Poly Dimethyl Siloxane, silicone) may be applied. In a block 935, a self-assembling layer may be applied. A packing procedure, see block 340 may be performed as well, and the manufacture procedure may be finished in a block 345.

Figure 10:
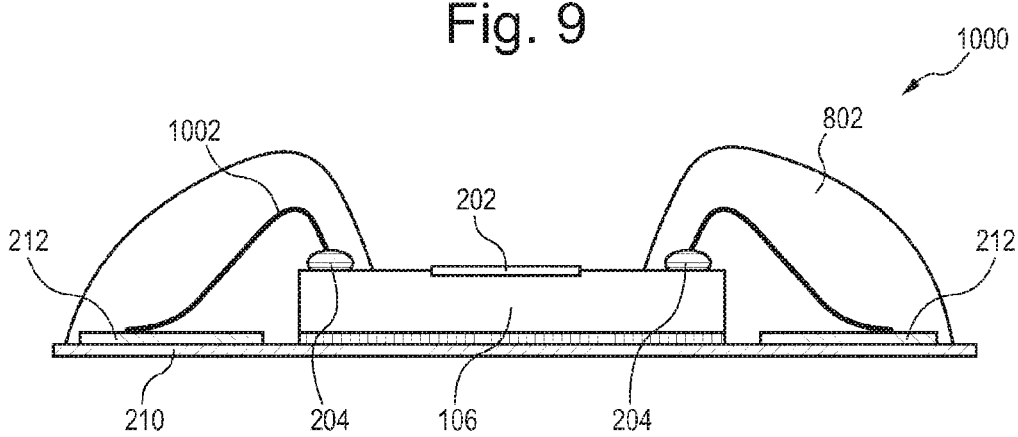
FIG. 10 illustrates a partially exposed and partially encapsulated sensor chip according to an exemplary embodiment of the invention.

The resulting product, a wire bond construction of a packaged sensor 1000, may look as shown in FIG. 10. A wire bond is denoted with reference numeral 1002.

Finally, it should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The words "comprising" and "comprises", and the like, do not exclude the presence of elements or steps other than those listed in any claim or the specification as a whole. The singular reference of an element does not exclude the plural reference of such elements and vice-versa. In a device claim enumerating several means, several of these means may be embodied by one and the same item of software or hardware. The mere fact that certain measures are recited in mutually different dependent claims does not indicate that a combination of these measures cannot be used to advantage.

The invention claimed is:

1. A sensor array for detecting particles, the sensor array comprising
   a substrate having a plurality of holes;
   a plurality of electronic sensor chips each having a sensor active region being sensitive to the presence of particles to be detected;
   an electric contacting structure adapted for electrically contacting the plurality of electronic sensor chips;
   wherein at least one of the plurality of electronic sensor chips and the electric contacting structure are connected to the substrate so that the plurality of holes in combination with at least one of the plurality of electronic sensor chips and the electric contacting structure form a plurality of wells with integrated particle sensors.

2. The sensor array of claim 1, wherein the plurality of holes include through holes.

3. The sensor array of claim 1, wherein each of the plurality of electronic sensor chips is adapted for evaluating a sensor signal, optionally, an electronic sensor signal, generated at the sensor active region in response to the presence of the particles to be detected.

4. The sensor array of claim 1, wherein a surface of each of the plurality of electronic sensor chips closes a respective one of the plurality of holes to thereby form a bottom of a respective one of the plurality of wells.

5. The sensor array of claim 1, wherein the electric contacting structure electrically interconnects different ones of the plurality of electronic sensor chips.

6. The sensor array of claim 1, wherein the electric contacting structure is a patterned foil comprising electrically conductive traces.

7. The sensor array of claim 1, further comprising bumps and/or wires electrically coupling the electric contacting structure to the plurality of electronic sensor chips.

8. The sensor array of claim 1, further comprising a sealing element for sealing an interface between the electric contacting structure and the electronic sensor chips.

9. The sensor array of claim 1, further comprising a communication interface electrically coupled to the electric contacting structure and adapted for providing electric sensor signals to a communication partner device couplable to the sensor array via the communication interface.

10. The sensor array of claim 1, wherein the substrate is a rigid plate.

11. The sensor array of claim 1, adapted as a microtiter plate having at least one of a pitch selected from 9 mm, 4.5 mm and 2.25 mm and one of 96, 384 and 1536 wells.

12. The sensor array of claim 1, adapted as a self-sufficiently operable portable sensor array.

13. The sensor array of claim 1, wherein at least a part of the plurality of electronic sensor chips is partially encapsulated by an encapsulant and is partially free of an encapsulation so that the sensor active region is exposed.

14. The sensor array of claim 1, wherein at least a part of the plurality of electronic sensor chips has a plurality of sensor active regions arranged in a finger configuration having at least one of a finger size and a pitch configured in order to fit in a microplate.

15. The sensor array of claim 1, whereas at least one of the group including an integrated circuit, a capacitor, and another electronic element is attached and electrically connected to the substrate.

16. A method of manufacturing a sensor array for detecting particles, the method comprising;
   providing a substrate having a plurality of holes;
   providing a plurality of electronic sensor chips each having a sensor active region being sensitive to the presence of particles to be detected;
   providing an electric contacting structure adapted for electrically contacting the plurality of electronic sensor chips;
   connecting at least one of the plurality of electronic sensor chips and the electric contacting structure to the substrate so that the plurality of holes in combination with at least one of the plurality of electronic sensor chips and the electric contacting structure form a plurality of wells with integrated particle sensors.

17. The method of claim 16, further comprising
   mounting the plurality of electronic sensor chips on the electric contacting structure to thereby form a continuous contacted chip arrangement; and
   subsequently connecting the continuous contacted chip arrangement to the substrate.

18. The method of claim 16, further comprising
   forming the electric contacting structure on the substrate to thereby form a continuous contacted substrate arrangement; and
   subsequently mounting the plurality of electronic sensor chips on the continuous contacted substrate arrangement.

19. The method of claim 16, further comprising
   moulding the electric contacting structure into a material constituting the substrate to thereby form a continuous contacted substrate arrangement; and
   subsequently mounting the plurality of electronic sensor chips on the continuous contacted substrate arrangement.

* * * * *